United States Patent
La Bianco et al.

(10) Patent No.: US 7,044,938 B2
(45) Date of Patent: May 16, 2006

(54) SKIN TREATMENT APPARATUS AND METHODS

(76) Inventors: Kerrie L. La Bianco, 12 Las Cruces, Irvine, CA (US) 92614; Richard A. La Bianco, 12 Las Cruces, Irvine, CA (US) 92614

( * ) Notice: Subject to any disclaimer, the term of this patent is extended or adjusted under 35 U.S.C. 154(b) by 235 days.

(21) Appl. No.: 10/197,971

(22) Filed: Jul. 17, 2002

(65) Prior Publication Data
US 2004/0015139 A1    Jan. 22, 2004

(51) Int. Cl.
*A61M 35/00* (2006.01)
*B43K 5/14* (2006.01)
*A61B 17/50* (2006.01)

(52) U.S. Cl. .................. 604/290; 604/289; 604/309; 401/133; 606/131

(58) Field of Classification Search ........ 606/131–133; 604/289, 290; 601/131, 80, 81, 135, 169
See application file for complete search history.

(56) References Cited

U.S. PATENT DOCUMENTS

| | | | | |
|---|---|---|---|---|
| 5,199,808 A | * | 4/1993 | Gueret | .......... 401/133 |
| 6,471,712 B1 | * | 10/2002 | Burres | .......... 606/131 |
| 2001/0018061 A1 | | 8/2001 | Rhoades | |
| 2001/0046506 A1 | | 11/2001 | Rhoades | |
| 2002/0041891 A1 | | 4/2002 | Cheski | |
| 2002/0087168 A1 | | 7/2002 | Winitsky | |

* cited by examiner

*Primary Examiner*—Tatyana Zalukaeva
*Assistant Examiner*—Melanie J Hand
(74) *Attorney, Agent, or Firm*—Brown Raysman Milstein Felder & Steiner LLP

(57) ABSTRACT

Apparatus for skin treatment using abrasion lotion with particulate includes an appliance and an applicator. The appliance includes a motor for actuating the applicator by rotating or oscillating. The applicator includes a surface made from a substantially unresilient or inabsorbent material for impressing and urging the particulate upon the skin. In operation, the abrasion lotion is applied either on the surface of the applicator or directly to the skin, the surface placed against skin, and the motor activated. When in motion, the surface impresses particulate of the lotion upon the skin and urges the impressed particulate across the skin abrading and exfoliating it. The surface may include a field and a plurality of bosses disposed on it with channels between adjacent bosses, or a relief field. When the applicator is in motion, the bosses urge and push the abrasion lotion, and the relief field vectors particulate upon the skin.

16 Claims, 9 Drawing Sheets

SKIN TREATMENT APPARATUS AND METHODS

BACKGROUND OF THE INVENTION

The present invention relates to skin treatment apparatus and methods.

Professional skin treatment procedures are expensive and time consuming. For example, microdermabrasion procedures require a patient to travel to a facility and undergo treatment by a certified professional utilizing specialized equipment. Such sessions involve pneumatic abrasion of the skin with microscopic crystals, such as aluminum oxide or magnesium oxide.

As an alternative to professional treatment sessions, home treatment typically involves facial scrubs or microdermabrasion creams applied by hand. Although time and money are saved, the quality of the treatment and the level of skin abrasion are sacrificed. Some commercially available products include those wherein a vibrating or spinning foam pad is used to apply cream to the face. However, the foam absorbs the cream and becomes clogged, wasting the expensive cream. In addition, the foam pad is highly resilient and pliant; therefore, a user needs to exert substantial pressure in attempting to effect abrasion. This pressure increases the friction between the pad and the skin, thereby generating heat and causing irritation.

Accordingly, there is a need in the art for methods and apparatus for effectively treating the skin with abrasion lotion that may be utilized economically and outside of a professional facility.

SUMMARY OF THE INVENTION

Apparatus for treating skin using abrasion lotion with particulate includes an appliance and an applicator. The appliance may include a motor for actuating the applicator, for example, by rotation or oscillation. The applicator may include an application surface for impressing particulate upon the skin and for urging the impressed particulate across skin when the application surface is contacting skin and the motor is activated. The application surface may be made from a substantially unresilient material or a substantially inabsorbent material, or both.

To treat skin, abrasion lotion may be applied either on the application surface of the applicator or directly on the skin. The application surface may then be placed against skin, and the motor may be activated. When in motion, the application surface impresses particulate upon the skin and urges the impressed particulate across the skin, thereby abrading and exfoliating the skin. The applicator may be moved over an area of the skin for complete treatment.

The application surface may include a field and a plurality of bosses disposed on the field, with channels defined between adjacent bosses. When the applicator is in motion and the surface contacts skin, the bosses urge and push the abrasion lotion into and through the channels, thereby moving and redistributing the abrasion lotion during operation. This impressing and urging of particulate, described as vectoring herein, exfoliates the skin. Alternatively, the application surface may include a relief field including a plurality of intaglios.

DETAILED DESCRIPTION OF THE INVENTION

Figure 1:
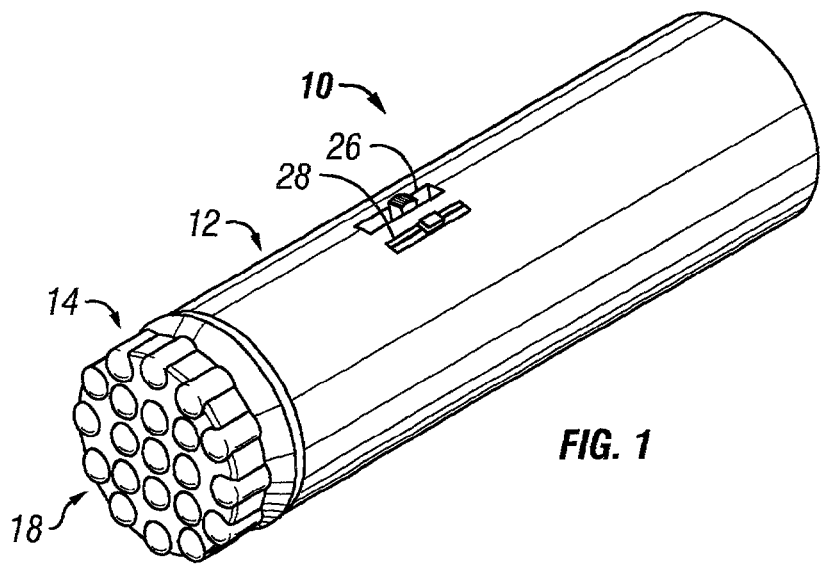
FIG. 1 is a perspective view of an appliance for treating skin using abrasion lotion.
Figure 2:
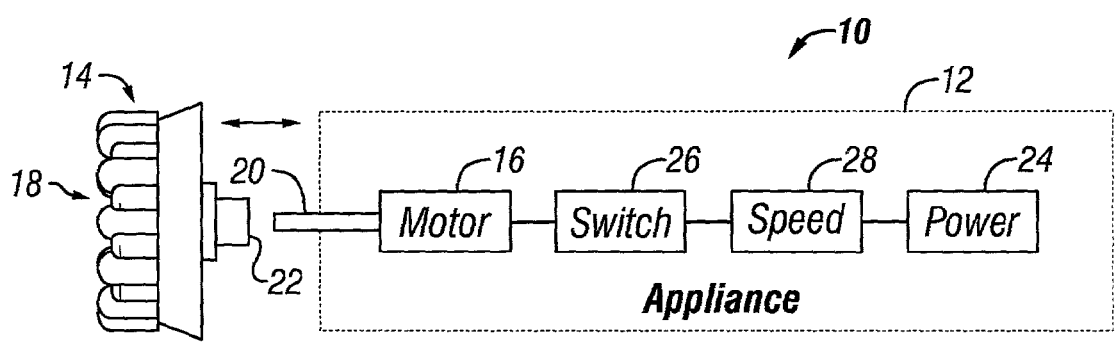
FIG. 2 schematically illustrates a block diagram of an appliance in relation to an applicator in side view.

Apparatus for treating skin using abrasion lotion with particulate is illustrated in FIGS. 1 and 2 and referenced generally with numeral 10. Exemplary apparatus 10 includes an appliance 12 and an applicator 14. The appliance 12 may include a motor 16 for actuating the applicator 14.

The applicator 14 may include an application surface 18 for impressing particulate upon skin and urging particulate across skin when the surface 18 is contacting skin and the motor 16 is activated. For the purposes of this description, this impressing and urging of particulate upon the skin will be known as "vectoring" particulate, which will be discussed in detail below.

In a number of embodiments the application surface 18 may be substantially unresilient so that deformation of the surface 18 is minimized under normal application pressure from a user against skin over soft tissue (i.e., not bone). In other embodiments the application surface 18 may be substantially inabsorbent so that absorption of the abrasion lotion by the surface 18 is minimized or prevented. In still other embodiments the application surface 18 may be both substantially unresilient and substantially inabsorbent.

In a number of embodiments, the appliance 12 may be configured to actuate the applicator 14 by rotation. In other embodiments, the appliance 12 may oscillate the applicator 14. In either case, the appliance 12 may include a shaft 20 to which a complementary base 22 of the applicator 14 is engageable. The applicator 14 may be either permanently attached to the appliance 12 or may be releasably attached (i.e., the shaft 20 and the base 22 are configured to be releasably engageable with each other).

As shown in FIG. 2, the appliance 12 may include a power supply 24 and a power switch 26 to activate the motor 16. The power supply 24 may be an AC power source or, in other embodiments, may be a DC source such as batteries, AC adapter, and so on. In a number of embodiments, the appliance 12 may include a speed control switch 28 for adjusting the speed of the motor 16. For example, the speed control switch 28 may adjust the speed of the motor 16 from a lower limit to an upper limit, e.g., 10 revolutions per minute (RPM) to 1,000 RPM in some of the rotary embodiments, or 10 oscillations per minute (OPM) to 1,000 OPM in some of the oscillation embodiments. The speed control switch 28 may vary the speed discretely or continuously.

Figure 3:
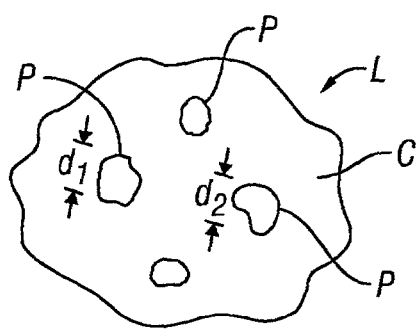
FIG. 3 illustrates abrasion lotion with suspended particulate.

As mentioned, the apparatus 10 treats skin using abrasion lotion with particulate. As shown in FIG. 3, abrasion lotion L includes particulate P that are suspended in a viscous carrier material C. Each particulate P has dimensions or breadth, which may be approximated for the purposes of this description by a diameter $d_1$, $d_2$, and so on, as shown in the figure. Accordingly, the size of the particulate P may be approximated as an average diameter of the type of particulate in the abrasion lotion.

In a number of embodiments, the abrasion lotion may be a microdermabrasion lotion or cream with a particulate size that depends upon the type of desired abrasion. For example, commercially available microdermabrasion creams may have a magnesium oxide particulate with a size on the order of about 40 micrometers (μm) to about 120 μm.

Figure 4:
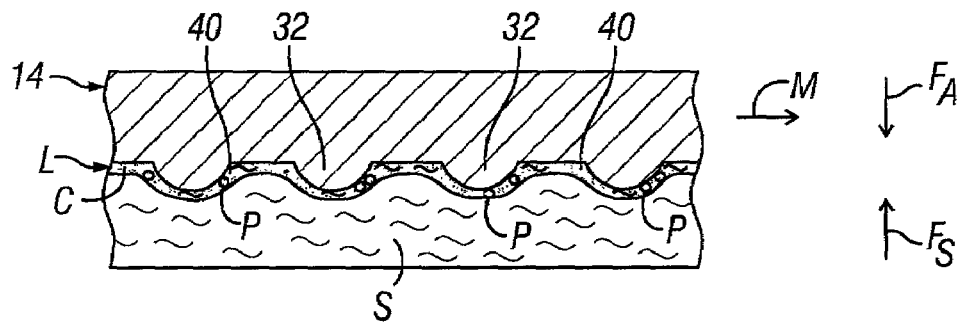
FIG. 4 is a cross-sectional view of an applicator with an application surface placed against skin with abrasion lotion therebetween (with the application surface also being a cross-sectional view taken along line 4—4 of FIG. 12)

To treat skin, abrasion lotion may be applied on the surface 18 of the applicator 14. In other embodiments, abrasion lotion may be applied the skin directly. The surface 18 may then be placed against skin S, as shown in FIG. 4. The motor 16 may then be activated. When in motion, the surface 18 impresses and urges particulate P across the skin S, thereby abrading the skin. For example, if the surface 18 (i.e., the applicator 14) moves in the direction indicated by arrow M, the particulate-grabbing surface 18 compresses against the skin S and urges abrasion lotion and particulate P to move against the skin, thereby abrading the surface of the skin. The applicator 14 may be moved over the skin to exfoliate a desired area of skin, e.g., the face.

Figure 5:
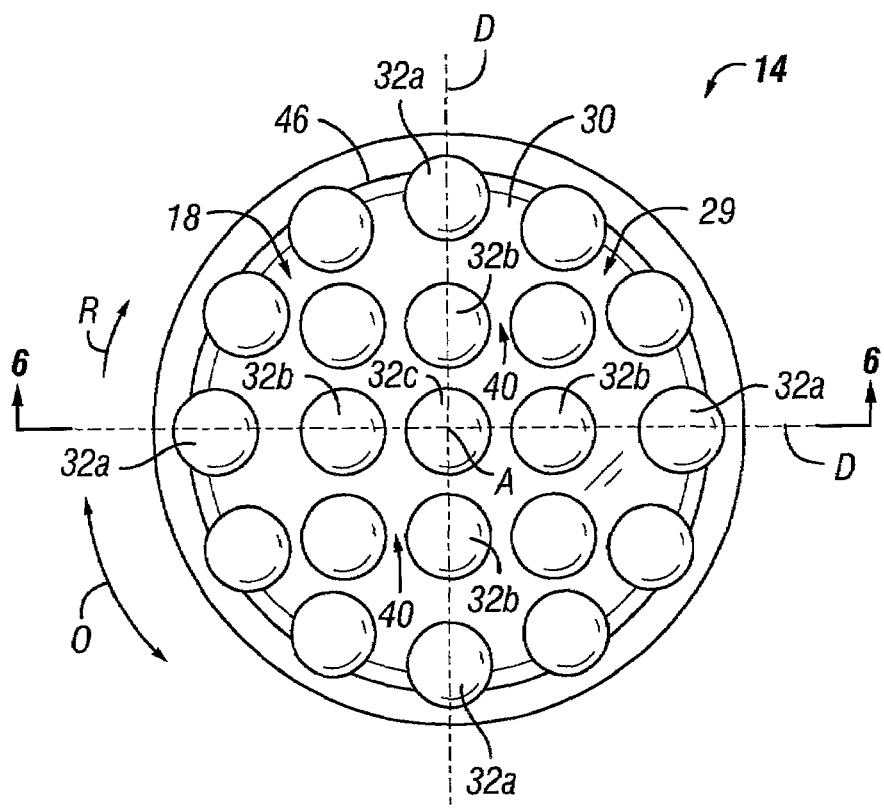
FIG. 5 is a plan view of an applicator surface with bosses on a field.
Figure 6:
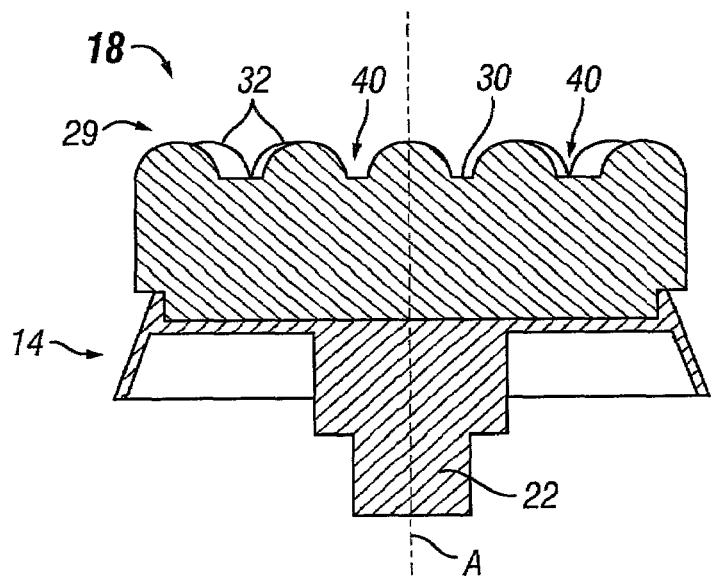
FIG. 6 is a cross-sectional view taken along 6—6 of FIG. 5.

In an exemplary embodiment shown in FIGS. 5 and 6, the applicator 14 includes the base 22 for engaging with the appliance 12 and the application surface 18 for impressing and urging particulate across skin when the surface 18 is contacting skin and the applicator is moving, e.g., rotating. In a number of embodiments, the surface 18 may include an embossed field 29. For example, the embossed field 29 may include a field 30 and a plurality of bosses 32 disposed on the field 30. In some embodiments, the bosses 32 may be arcuate in profile or section. In other embodiments, one of which is shown in FIG. 6, the bosses 32 may be dome shaped or hemispherically shaped.

Figure 7:
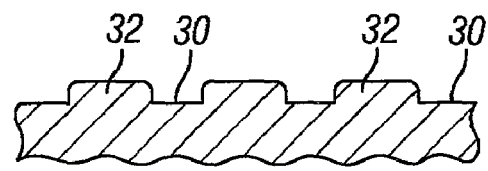
FIG. 7 is a cross-section view of bosses disposed on a field.
Figure 8:
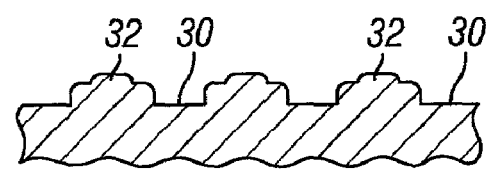
FIG. 8 is a cross-section view of bosses disposed on a field according to another embodiment.
Figure 9:
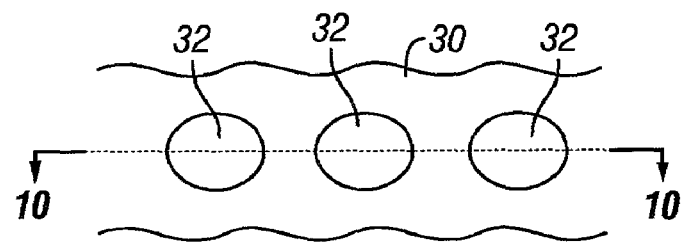
FIG. 9 is a plan view of bosses disposed on a field according to still another embodiment.
Figure 10:
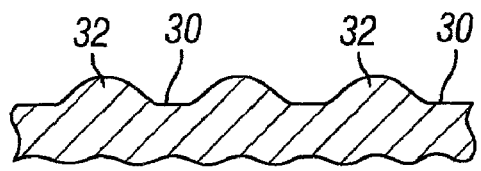
FIG. 10 is a cross-sectional view taken along 10—10 of FIG. 9.
Figure 11:
FIG. 11 is a cross-section view of bosses disposed on a field according to yet another embodiment.

In still other embodiments, the bosses 32 may be plateau shaped or rectilinear in section, as shown in FIG. 7. In some embodiments, such as shown in FIG. 8, the bosses 32 may include a plurality of discontinuities 34 defined by stepping the bosses. In embodiments exemplified in FIGS. 9 and 10, in other embodiments, the bosses 32 may be voids in plan view as shown in FIG. 9. and arcuate in section as shown in FIG. 10. In still other embodiments, the bosses 32 may have concave sides 36 so that a peak 38 is formed, as shown in FIG. 11.

In many embodiments, the surface 18 of the applicator 14 may be made from a substantially hard or unresilient material, which material may be, e.g., rubber, plastic, or metal. For example, in embodiments where the application surface 18 is made from silicone rubber, the hardness of the surface 18 may range from about 30 to about 60 on the Shore A scale. Alternatively, in embodiments where the application surface 18 is made from plastic or hard rubber, the hardness of the surface 18 may range from about 40 to about 80 on the Shore A scale.

For the purposes of this description, "substantially unresilient" material does not deform when pressed against skin over soft tissue such as muscle, e.g., the cheeks. That is, the skin will deform prior to the application surface 18 when the surface is pressed against the skin. In addition, "substantially unresilient" material will deform slightly when pressed against skin over hard tissue such as bone, e.g., the nose bridge or forehead. In some embodiments, substantially unresilient material may include material with a hardness of at least about two times the hardness of skin on the Shore A scale. As skin has a hardness of about 10 on the Shore A scale, then in these embodiments the application surface 18 may have a hardness of at least 20 on the Shore A scale.

In other embodiments, the surface 18 may be made from a pliant or relatively resilient material such as rubber. For example, in the embodiment shown in FIG. 11, each of the bosses 32 may be pliant so that trauma to the skin caused by the peaks 38 is minimized. In pliant embodiments, the surface 18 may be made from a material with a hardness at the lower end of the Shore A scale, e.g., less than 30.

In still other embodiments, the surface 18 of the applicator 14 may be made from a non-porous or inabsorbent material so that abrasion lotion does not build-up within or is not absorbed by the applicator 14.

Figure 23:
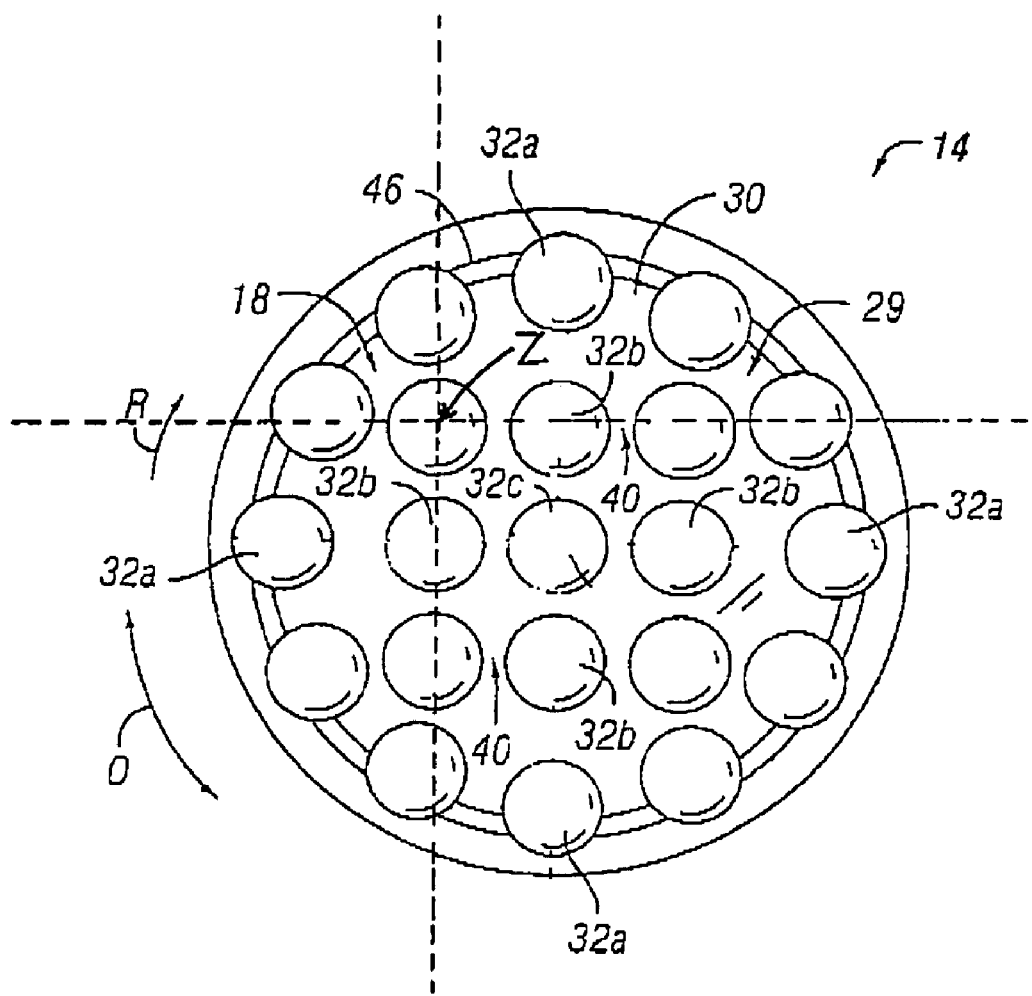
FIG. 23 is a plan view of an applicator surface with bosses on a field.
Figure 24:
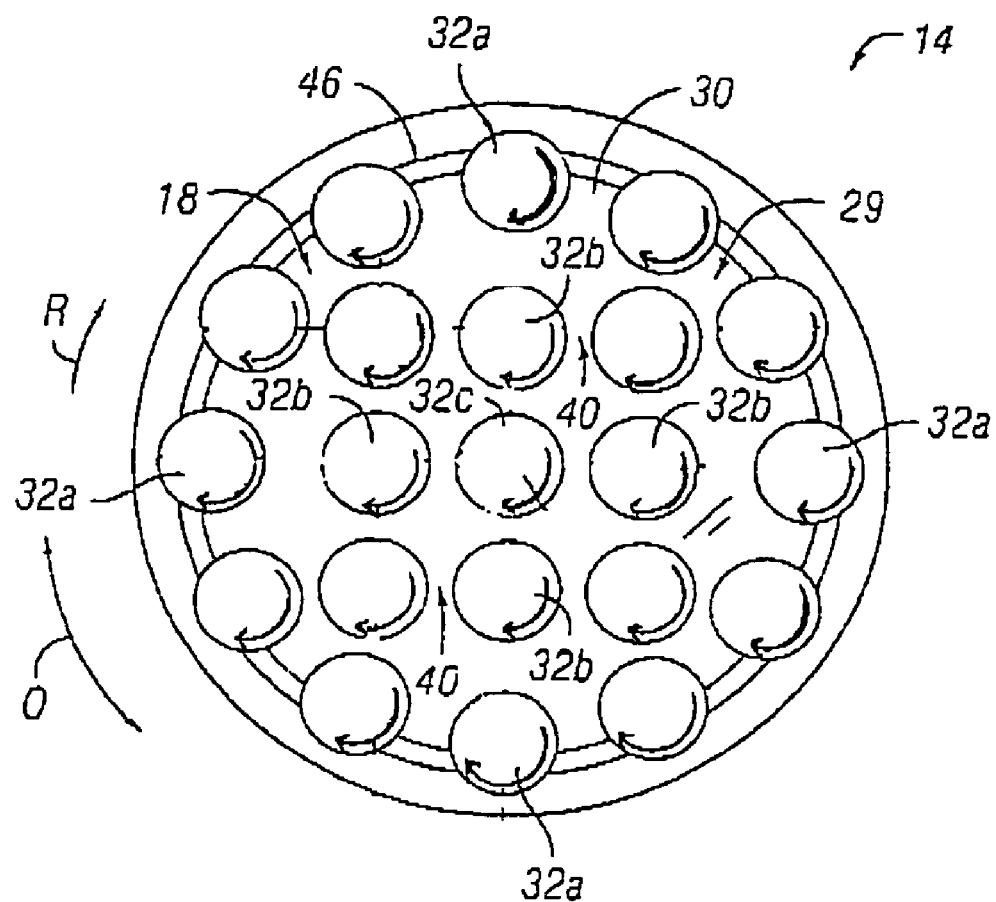
FIG. 24 is a plan, view of an applicator surface with bosses on a field to show movement analogous to an orbital sander.

Referring to FIGS. 5 and 6, in some of the embodiments, the applicator 14 may be circular. In rotary embodiments, the applicator 14 may rotate about an axis A as shown by arrow R or may oscillate about axis A as shown by arrow O. In other embodiments, the applicator 14 may oscillate in a circular pattern analogous to an orbital sander. FIG. 23 is a plan view of an orbital sander, according to one embodiment of the present invention. In this embodiment, the applicator 14 may rotate about an off-centered axis Z as shown by arrow R or may oscillate about axis Z as shown by arrow O. FIG. 24 is a plan view of applicator 14 to illustrate the small orbital circular paths taken by each boss 32a, 32b, and 32c when the applicator rotates as shown by arrow R. It should be noted that the rotational axis of the applicator may be located at A as seen in FIG. 5 or off-centered at Z as seen in FIG. 23. Each boss traces a small circular path shown by the arrow within each boss when the applicator 14 traces a rotational path when viewed looking directly down on the applicator from above.

As shown in FIGS. 4 and 6, channels 40 may be defined between adjacent bosses 32. When the applicator 14 is in motion and the surface 18 contacts skin, the bosses 32 urge and push the abrasion lotion L into and through the channels 40, thereby moving and redistributing the abrasion lotion during operation. In addition, skin cells that are abraded during treatment may be received within the channels 40.

Regarding exfoliation and abrasion in more detail, the applicator 14 may be pressed against skin S with sufficient force to deform the skin, as indicated by arrow $F_A$ in FIG. 4. Under compression, the skin in turn exerts a force against the bosses 32, as indicated by arrow $F_S$. As mentioned above, in a number of embodiments the application surface 18 including the bosses 32 may be substantially unresilient so that the applied forces do not deform the bosses 32.

Figure 12:
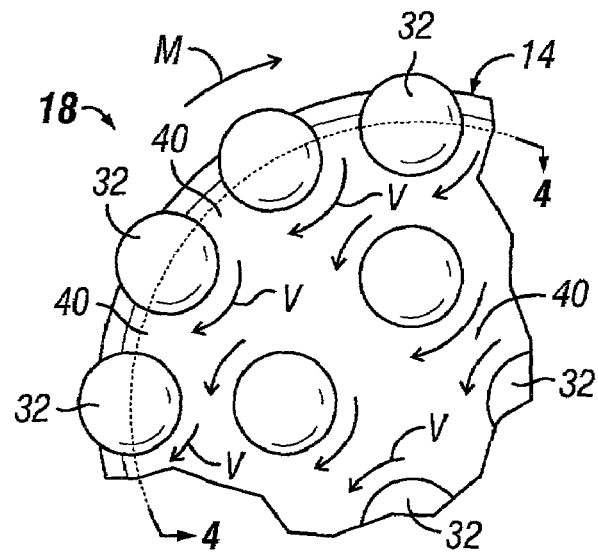
FIG. 12 is a fragmentary plan view illustrating the movement of abrasion lotion by bosses of an applicator when applied against skin.

With additional reference to FIG. 12, when the applicator 14 is pressed against the skin and is moving in a direction indicated by arrow M, the bosses 32 move through the abrasion lotion L positioned between the applicator 18 and the skin S and impress particulate P upon the skin. In addition to being compressed between the bosses 32 and the skin S as shown in FIG. 4, the lotion is forced around the bosses 32 and through the channels 40 as the applicator 14 is moving, which is indicated by arrows V in FIG. 12.

Figure 13:
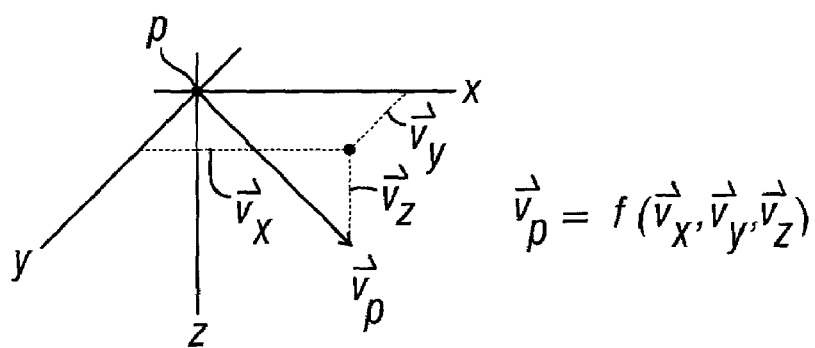
FIG. 13 illustrates the concept of vectoring particulate upon skin.

As mentioned above, this movement of the lotion and particulate by the bosses 32 is known as vectoring. As shown in FIG. 13, a particulate P is both impressed upon the skin and urged across the skin, the forces of which may be in three dimensions. In the representative Cartesian coordinate system shown in FIG. 13, the impressing of the particulate upon the skin may be represented by vector $V_z$. The urging of the particulate across the skin may be represented by vectors $V_x$ and $V_y$. Accordingly, the overall movement of a particulate P may be represented by vector $V_P$ which is a function of vectors $V_x$, $V_y$ and $V_z$. Therefore, the application surface 18 vectors particulate across the skin to abrade dead cells and to exfoliate the skin.

In a number of embodiments the bosses 32 may be disposed on the field 30 such that when the applicator 14 is rotating about axis A, spatial paths of rotation are defined. More specifically, with reference to FIG. 14, when rotating, the surface 18 may have defined an occupied orbit 42 wherein one or more of the bosses 32 occupies and follows a spatial path of rotation about the axis A. In addition, the surface 18 may have defined a vacant orbit 44 wherein not one of the bosses 32 occupies a spatial path of rotation about the axis A.

Figure 14:
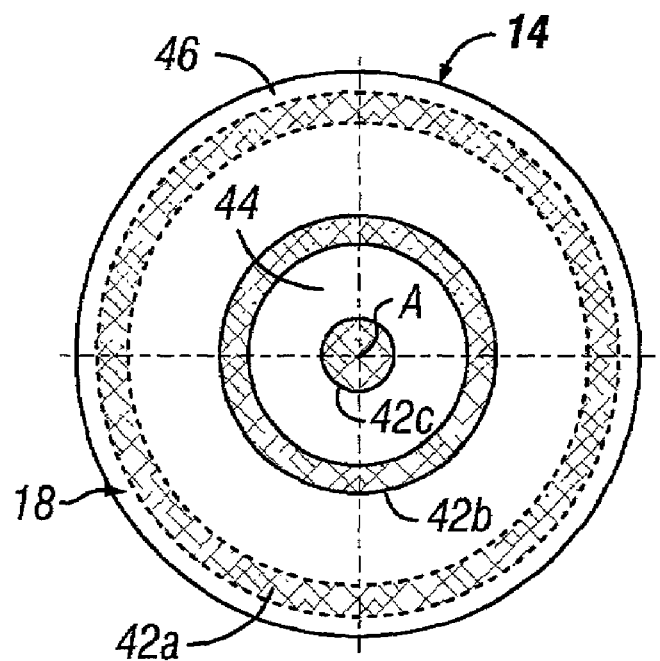
FIG. 14 illustrates spatial paths of rotation of bosses of an applicator.

For example, in the embodiment shown in FIG. 5, bosses 32a disposed about a periphery 46 of the surface 18 define occupied orbit 42a of FIG. 14; bosses 32b define occupied orbit 42b; and boss 32c disposed at the axis A defines occupied orbit 42c. In a number of embodiments, occupied orbits may overlap each other radially (not shown in FIG. 14). Accordingly, for the embodiment shown in FIG. 5, a vacant orbit 44 is defined adjacent to boss 32c disposed at the axis A and its corresponding occupied orbit 42c. For the purposes of this description and for clarity, FIG. 14 represents only three occupied orbits 42 although a plurality of overlapping occupied orbits may be implemented.

The bosses 32 may be disposed on the field 30 in any number of patterns and configurations. For example, as shown in FIG. 5, a plurality of the bosses 32 are respectively disposed along a pair of perpendicular diameters D of the surface 18. In addition, the bosses 32 may be randomly disposed on the field 30. The bosses 32 may be disposed in regular concentric rings or in a swirl or spiral.

Figure 15:
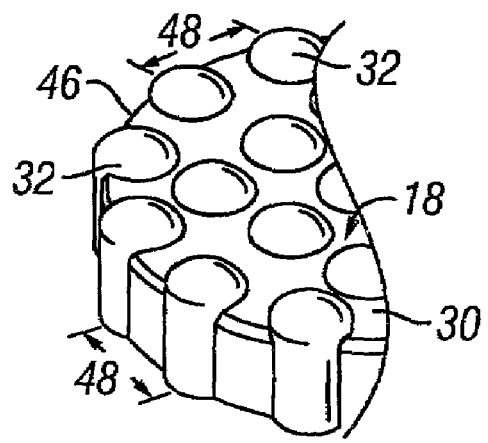
FIG. 15 is a fragmentary perspective view of an applicator with protruding peripheral bosses.

Referencing FIG. 15, in a number of embodiments, one or more of the bosses 32 may protrude beyond the periphery 46 of the surface 18. Accordingly, in rotary embodiments, an occupied orbit 42 is radially outmost path of rotation for the surface 18. In other embodiments, the field 30 between adjacent bosses 32 disposed about the periphery 46 of the surface 18 is radially recessed, thereby forming gaps 48.

Figure 16:
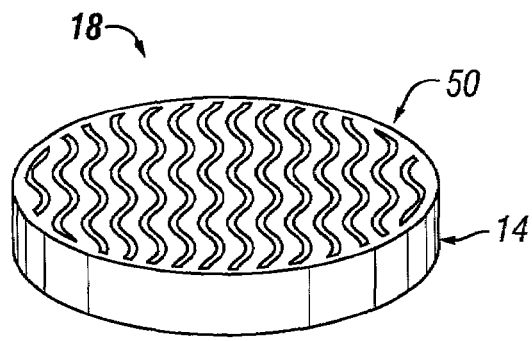
FIG. 16 is a perspective view of an applicator with a particulate-grabbing surface having a relief field.
Figure 17:
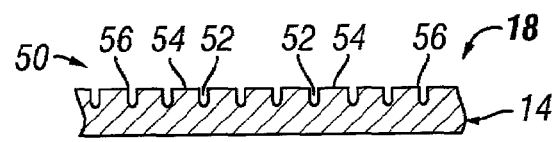
FIG. 17 is an enlarged cross-sectional view of a relief surface.

Referring to FIGS. 16 and 17, the application surface 18 of the applicator 14 may include a relief or intaglio field 50. In some embodiments, the relief field 50 includes troughs 52 defined between ridges 54. Accordingly, a discontinuity 56 may be defined between each trough 52 and ridge 54. Particulate in the abrasion lotion may be received or partially received in the troughs 52, retained by a discontinuity 56, and urged against skin by the ridges 54 during motion of the applicator 14. In a number of embodiments, the troughs 52 may have a depth less than the diameter of the particulate so that particulate does not accumulate within the troughs.

Figure 18:
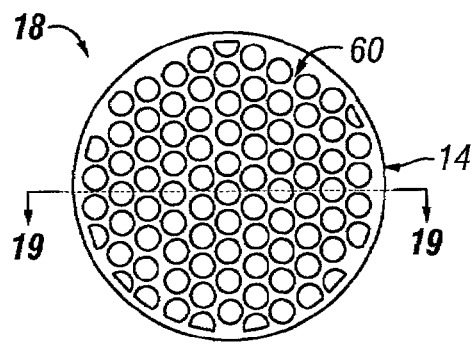
FIG. 18 is a plan view of another embodiment of a relief surface.
Figure 19:
FIG. 19 is a cross-sectional view of a relief surface taken along line 19—19 of FIG. 18.
Figure 20:
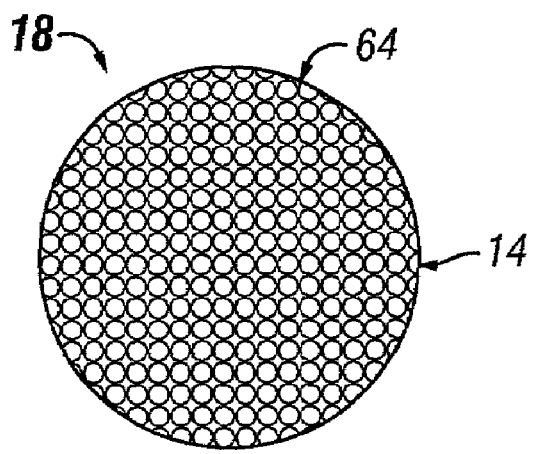
FIG. 20 is a plan view of yet another embodiment of a relief surface.
Figure 21:
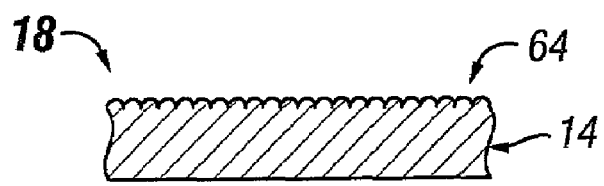
FIG. 21 is a fragmentary cross-sectional view of a relief surface of FIG. 20.

Referring to FIGS. 18 and 19, the application surface 18 may be arcuate in section, for example, concave as shown in the figures. In some embodiments, the application surface 18 may be a dimpled or pockmarked field 60 with a plurality of dimples or pocks 62. In still other embodiments, the application surface 18 may include a boss field 64 as shown in FIGS. 20 and 21. The boss field 64 may spatially occupy the entire contact surface of the applicator 14.

In other embodiments, the relief field 50 may be a mottled surface of bosses and ridges. The relief field 50 may be formed as a regular pattern or may be a random pattern. In other embodiments, the relief field 50 may be configured analogous to a fingerprint pattern. In still other embodiments, the field 30 on which the bosses 32 are disposed (see FIG. 5) may include particulate-grabbing relief.

Figure 22:
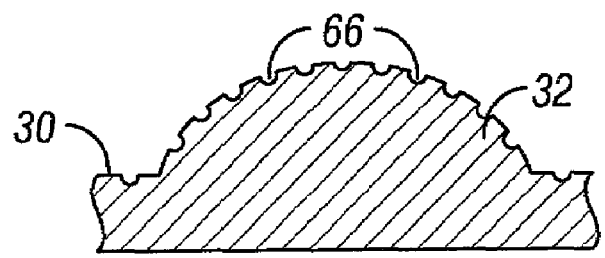
FIG. 22 is an enlarged cross-sectional view of a boss including a relief surface.

In addition, the surface of the bosses 32 may include particulate-grabbing relief. For ex ample, as shown in FIG. 22, one or more of the bosses 32 may include discontinuities or intaglios 66 are formed thereon to enhance the urge of the particulate. The intaglios 66 may be discrete, for example, analogous to the pocks 62 shown in FIG. 19, or may be linear, for example, analogous to the troughs 52 shown in FIG. 17.

In production, the applicator 14 may be cast, machined, or injection molded. In the embodiments including a relief field 50, the mold or cast may be etched, e.g., with acid, a laser, or a machine, to form the relief field. Alternatively, any relief field may be etched or formed after the applicator 14 has been molded or cast. Pocks, dimples, intaglios, and other particulate-grabbing discontinuities may be formed by etching, either chemical, physical (e.g., "sand" blasting), or laser.

Those skilled in the art will understand that the preceding exemplary embodiments of the present invention provide the foundation for numerous alternatives and modifications thereto. These and other modifications are also within the scope of the present invention. Accordingly, the present invention is not limited to that precisely as shown and described above but by the scope of the appended claims.

What is claimed is:

1. An applicator for treating skin using abrasion lotion with particulate, the applicator for use with an appliance configured to move the applicator, the applicator comprising:
- a base for engaging with the appliance; and
- a substantially unresilient application surface that vectors particulate upon skin when the surface is contacting skin and the applicator is moving;
- wherein the application surface includes an embossed field having a plurality of bosses and wherein a plurality of the bosses are disposed about a periphery of the application surface and at least one of the bosses protrudes beyond the periphery of the application surface.

2. An applicator as claimed in claim 1 wherein the bosses are arcuate in section.

3. An applicator as claimed in claim 1 wherein the appliance rotates the applicator and wherein the applicator rotates about an axis and channels are defined between adjacent bosses;
- the bosses urging abrasion lotion through the channels when the application surface is contacting skin and the applicator is rotating.

4. An applicator as claimed in claim 1 wherein the bosses include a plurality of intaglios.

5. An applicator as claimed in claim 1 wherein the application surface includes a relief field.

6. An applicator as claimed in claim 5 wherein the relief field includes troughs defined between ridges.

7. An applicator as claimed in claim 6 wherein the particulate of the abrasion lotion has a diameter and wherein the troughs have a depth less than the diameter of the particulate.

8. An applicator for treating skin using abrasion lotion with particulate, the applicator for use with an appliance configured to move the applicator, the applicator comprising:
- a base for engaging with the appliance; and
- a substantially inabsorbent application surface that vectors particulate upon the skin when the surface is contacting skin and the applicator is moving wherein the application surface includes an embossed field having a plurality of bosses;
- wherein a plurality of the bosses are disposed about a periphery of the application surface and wherein at least one of the bosses protrudes beyond the periphery of the application surface.

9. An applicator as claimed in claim 8 wherein the bosses are arcuate in section.

10. An applicator as claimed in claim 8 wherein the appliance rotates the applicator and wherein the applicator rotates about an axis and channels are defined between adjacent bosses;
- the bosses urging abrasion lotion through the channels when the application surface is contacting skin and the applicator is rotating.

11. An applicator as claimed in claim 8 wherein at least one of the bosses protrudes beyond the periphery of the application surface.

12. An applicator as claimed in claim 8 wherein the application surface includes a relief field.

13. An applicator as claimed in claim 12 wherein the relief field includes troughs defined between ridges.

14. An applicator as claims in claim 13 wherein the particulate of the abrasion lotion has a diameter and wherein the troughs have a depth less than the diameter of the particulate.

15. An applicator for treating skin using abrasion lotion with particulate, the applicator for use with an appliance configured to move the applicator, the applicator comprising:
- a base for engaging with the appliance;
- a substantially unresilient application surface for vectoring particulate upon skin when the surface is contacting skin and the applicator is moving;
- the application surface includes an embossed field having a plurality of bosses; the plurality of bosses are disposed about a periphery of the application surface; and
- at least one of the bosses protrudes beyond the periphery of the application surface.

16. An applicator for treating skin using abrasion lotion with particulate, the applicator for use with an appliance configured to move the applicator, the applicator comprising:
- a base for engaging with the appliance;
- a substantially inabsorbent application surface for vectoring particulate upon skin when the surface is contacting skin and the applicator is moving;
- the application surface includes an embossed field having a plurality of bosses;
- the plurality of bosses are disposed about a periphery of the application surface; and
- at least one of the bosses protrudes beyond the periphery of the surface.

* * * * *